(12) United States Patent
Sofia et al.

(10) Patent No.: US 7,897,174 B2
(45) Date of Patent: Mar. 1, 2011

(54) FORMULATION COMPRISING BIOACTIVE AGENTS AND METHOD OF USING SAME

(75) Inventors: Susan J. Sofia, Methuen, MA (US); Daniel Schwartz, Lauf an der Pegnitz (DE); Wolfgang Friess, Iffeldorf (DE)

(73) Assignees: University of Erlangen-Nurnberg, Erlangen (DE); Wyeth Inc., Madison, NJ (US)

( * ) Notice: Subject to any disclaimer, the term of this patent is extended or adjusted under 35 U.S.C. 154(b) by 0 days.

(21) Appl. No.: 10/361,263

(22) Filed: Feb. 10, 2003

(65) Prior Publication Data

US 2003/0223983 A1 Dec. 4, 2003

Related U.S. Application Data

(60) Provisional application No. 60/355,135, filed on Feb. 8, 2002.

(51) Int. Cl.
*A61K 9/14* (2006.01)

(52) U.S. Cl. .................................. 424/484; 424/489

(58) Field of Classification Search ................ 530/350, 530/399; 514/2, 12, 21, 54; 435/69.1; 424/198.1, 424/602, 450, 490
See application file for complete search history.

(56) References Cited

U.S. PATENT DOCUMENTS

| | | | |
|---|---|---|---|
| 5,013,649 A * | 5/1991 | Wang et al. | 435/69.1 |
| 5,171,579 A | 12/1992 | Ron et al. | 424/486 |
| 5,385,887 A | 1/1995 | Yim et al. | 514/12 |
| 5,618,924 A | 4/1997 | Wang et al. | 530/399 |
| 5,948,428 A * | 9/1999 | Lee et al. | 424/426 |
| 6,150,328 A * | 11/2000 | Wang et al. | 514/12 |
| 6,187,742 B1 * | 2/2001 | Wozney et al. | 514/2 |
| 6,190,880 B1 * | 2/2001 | Israel et al. | 435/69.1 |
| 6,287,588 B1 | 9/2001 | Shih et al. | 424/426 |
| 6,504,079 B2 * | 1/2003 | Tucker et al. | 623/16.11 |
| 6,559,119 B1 * | 5/2003 | Burgess et al. | 514/2 |
| 6,696,410 B1 * | 2/2004 | Lee et al. | 514/2 |
| 7,056,882 B2 * | 6/2006 | Kuberasampath et al. | 514/2 |
| 7,622,139 B2 * | 11/2009 | Li et al. | 424/601 |
| 7,671,012 B2 * | 3/2010 | Zamora et al. | 514/2 |
| 2002/0187104 A1 * | 12/2002 | Li et al. | 424/44 |
| 2003/0032098 A1 * | 2/2003 | Young et al. | 435/69.1 |
| 2003/0203038 A1 * | 10/2003 | Vail | 424/490 |
| 2003/0223983 A1 * | 12/2003 | Sofia et al. | 424/94.63 |
| 2005/0008620 A1 * | 1/2005 | Shimp et al. | 424/93.7 |
| 2007/0098756 A1 * | 5/2007 | Behnam | 424/423 |
| 2007/0110820 A1 * | 5/2007 | Behnam | 424/549 |
| 2007/0202144 A1 * | 8/2007 | Hellerbrand et al. | 424/423 |
| 2009/0130173 A1 * | 5/2009 | Behnam et al. | 424/426 |
| 2009/0155366 A1 * | 6/2009 | Pohl et al. | 424/486 |
| 2009/0214653 A1 * | 8/2009 | Birr et al. | 424/488 |
| 2010/0074876 A1 * | 3/2010 | Li et al. | 424/93.7 |
| 2010/0129415 A1 * | 5/2010 | Kinnane et al. | 424/423 |

FOREIGN PATENT DOCUMENTS

| | | |
|---|---|---|
| WO | WO 93/06872 | 4/1993 |
| WO | WO 95/07108 | 3/1995 |
| WO | WO 96/40074 | 12/1996 |
| WO | WO 03/066000 A2 * | 8/2003 |

OTHER PUBLICATIONS

Mundy, Advanced Drug Delivery Reviews, 2000, 42:165-173.*
Laurencin et al, biomaterials, 2001, 22:1271-1277.*
Saito et al, Bones, 2003, 32:381-386.*
Friess et al, Pharmaceutical Development and Technology, 1999, 4/3:387-396.*
Kokubo et al, Biomaterials, 2003, 24:1643-1651.*
Itoh et al, J. Vet. Med. Sci., 1998, 60/4:451-458.*
Yokota et al, International J. Pharmaceutics, 2001, 223:69-79.*
Patel et al, Biomaterials, 2001, 22:2081-2086.*
Boyan et al, J. Biomed. Mater. Res., 1999, 46:551-59.*
Bessho et al, J. Biomed. Mater. Res., 2002, 61:61-65.*
Ruhe et al, J. Bone Joint Surg. Am., 2003, 85-A Suppl. 3:75-81.*
Saito et al, J. Bone Joint Surg. Am., 2001, 83-A Suppl.1(Pt 2):S92-S98.*
Isobe et al, J. Biomed. Mater. Res., 1999, 45:36-41.*
Schrier et al, Pharmaceutical Development and Technology, 1999, 4/4:611-621.*
Schrier et al, AAPS PharmSciTech. 2001, 2/3:E17.*
Schrier et al AAPS PharmSciTech. 2001, 2/3:E18.*
Jin et al, Connective Tissue Research, 2004, 45/1:50-59.*
Winn et al, Clin. Orthop. and Related Research, 1999, 367 Suppl:S95-S106.*

(Continued)

*Primary Examiner*—N. M Minnifield
(74) *Attorney, Agent, or Firm*—Mintz Levin Cohn Ferris Glovsky and Popeo, P.C.; Ivor R. Elrifi; David E. Johnson, Esq.

(57) ABSTRACT

Disclosed are methods of making BMP-2 microparticles and methods of using the microparticles. These microparticles are prepared, for example, by mixing a solution containing BMP-2 with a second solution whose ionic concentration and pH results in the precipitation of the BMP-2.

14 Claims, 8 Drawing Sheets

OTHER PUBLICATIONS

Kirker-Head et al, Clinical Orthopaedics and Related Resaerch, 1998, 349:205-217.*
Wikesjo et al, Clin. Implant Dent. Relat. Res., 2003, 5/2:112-123.*
Ueki et al, J. Craniomaxillofac. Surgery, 2003, 31/2:107-114.*
Isobe et al, J. Oral Maxillofac. Surg., 1999, 57:695-698.*
Lee et al, J. Periodontol., 2003, 74/6:865-872.*
Friess et al, Pharmaceutical Research, Nov. 1997, 14/11 Suppl. p. S155.*
Zegzula et al, J. Bone and Joint Surgery, 1997, 79-A/12:1778-1790.*
Duggirala et al, Pharmaceutical Development and Technology, 1996, 1/1:11-19.*
Matin et al, International J. Oral Maxillofac Implants, 2003, 18:211-217.*
Wikesjo et al, Clin. Oral Implant Res., 2004, 15:194-204.*
Geiger et al, Advanced Drug Delivery Reviews, 2003, 55:1613-1629.*
Fairlie et al, Gene, 2000, 254:67-76.*
Winn et al, Advanced Drug Delivery Reviews, 1998, 31:303-318.*
Kang et al, Gene Therapy, 2004, 11:1312-1320.*
Arosarena et al, Orthod. Craniofacial Res., 2005, 8:267-276.*
Kofron et al, Current Opinion in Biotechnology, 2004, 15:399-405.*
Zilberman et al, Polymers for Advanced Technologies, 2002, 13:863-870.*
Govender et al, J. Bone and Joint Surgery-Series A, Dec. 2002, 84/12:2123-2134.*
Akamaru et al, Spine, Mar. 2003, 28/5:429-434.*
Yang, Dissertation Abstracts International, 2002, 65/1C:137.*
Oldham et al, J. Biochemical Engineering, 2000, 122:289-292.*
Crofts et al. J. Controlled Release, 1995, 35:91-105.*
Agrawal et al, J. Biomed. Mater. Res., 2001, 55:141-150.*
Ishaug et al, J. Biomedical Materials Research, 1994, 28:1445-1453.*
Valimeki et al, Tissue Engineering, 2005, 11/3-4:387-394.*
Neuwirth et al, Arthritis Research and Therapy, 2006, 8:R92, pp. 1-9.*
Patel et al, Acta Biomaterialia, 2008, 4:1126-1138.*
International Search Report for PCT/US03/03809, mailed Aug. 15, 2005.

* cited by examiner

FIG. 5
Lyophilisation – Drying Process

FORMULATION COMPRISING BIOACTIVE AGENTS AND METHOD OF USING SAME

RELATED APPLICATIONS

This application claims priority to U.S. Ser. No. 60/355,135, filed Feb. 8, 2002. The contents of this application are incorporated herein by reference in their entirety.

FIELD OF THE INVENTION

The invention relates generally to compositions containing bioactive agents such as bone morphogenetic protein-2 (BMP-2) and methods of making and using these compositions.

BACKGROUND OF THE INVENTION

Proteins used as therapeutic agents are typically provided as pharmaceutical compositions that can vary depending on, for example, the properties of the protein and the manner in which it will be introduced into a patient.

Protein instability can be a major difficulty in preparing these pharmaceutical compositions. Unwanted stresses on the protein during preparation of a pharmaceutical formulation can result in unwanted effects such as protein denaturation, precipitation, or adsorption to surfaces.

Pharmaceutical compositions containing bone morphogenetic protein 2 (BMP-2) are of great interest because this protein has been demonstrated to be involved in a variety of biologically important processes such as initiating bone growth and promoting wound healing. For example, BMP-2 has been used to treating or preventing a variety of bone-associated disorders, including those associated with the tibia, maxillofacial, and spinal bone.

BMP-2 is a member of the transforming growth factor-β superfamily. The mature protein is a disulfide-linked homodimer glycoprotein of 32-kilo daltons (kDa). BMP-2 shows limited solubility in water. This limited solubility can hinder attempts to develop pharmaceutical compositions containing this protein.

SUMMARY OF THE INVENTION

The invention is based in part on the discovery that microparticles containing precipitated bioactive agents can be conveniently prepared and resuspended in an aqueous solution prior to administration to a subject. An exemplary bioactive agent disclosed herein is a BMP-2 protein. The BMP-2 polypeptide can be either resolubilized or resuspended in the aqueous solution in a bioactive form, and the resolubilized or resuspended BMP-2 microparticle can thus be used to treat or prevent disorders or conditions in which BMP-2 has been demonstrated to be effective.

If desired, the BMP-2 solution of the added precipitation solution may contain a suitable biodegradable polymer, including, without limitation, hyaluronic acid, collagen, carmellose sodium, polyvinyl alcohol, chitosan or cationic starch. Accordingly, in one aspect, the invention provides a purified microparticle that includes precipitated bioactive bone morphogenetic proteins. A preferred bone morphogenetic protein is bone morphogenetic protein 2 (BMP-2). In some embodiments, the BMP-2 protein has an amino acid sequence of a human BMP-2 and/or is a recombinantly expressed protein. A preferred BMP-2 protein is recombinant human BMP-2 protein (rhBMP-2). The microparticle may in addition include additional agents beneficial for the treatment of the bone and/or cartilage defect, wound, or tissue.

In various embodiments, the microparticle has a diameter from about 0.1 μm to about 2000 μm. For example, suitable microparticle diameters can range, without limitation, from 0.5 μm to about 1500 μm, 1 μm to about 1000 μm, 5 μm to about 750 μm, 10 μm to about 500 μm, 15 μm to about 250 μm, 25 μm to about 125 μm, and 37 μm to about 75 μm. Other suitable ranges include, without limitation, 0.5 μm to about 140 μm, 5 μm to about 85 μm, about 15 μm to about 75 μm, or about 25 μm to about 50 μm.

If desired, the BMP-2 microparticle can be provided as a lyophilized formulation. In some embodiments, the microparticle is provided as an aqueous formulation.

In some embodiments, the microparticle is provided in association with a polymeric carrier. The polymeric carrier is preferably biodegradable.

Suitable polymeric carriers include, without limitation, polylactide, polylactide-co-glycolide, polyanhydride, polyorthoester, polyethylenevinylacetate, or nylon.

Also included within the invention is a pharmaceutical composition that includes a precipitated bioactive bone morphogenetic protein 2 (BMP-2) microparticle and a pharmaceutically acceptable carrier. The pharmaceutical composition preferably also includes resolubilized BMP-2 protein.

Also featured by the invention is a method of increasing bone morphogenetic protein-2 (BMP-2) levels in a subject. The method comprises providing an aqueous BMP-2 suspension that includes a resolubilized BMP-2 polypeptide introducing the aqueous suspension into the subject in an amount sufficient to increase BMP-2 levels in the subject.

In preferred embodiments, the aqueous suspension is prepared by introducing into an aqueous solution a microparticle that includes a precipitated bioactive bone morphogenetic protein 2 (BMP-2), and allowing the precipitated BMP-2 protein to form a suspension or to resolubilize, thereby preparing the aqueous BMP-2 suspension.

In some embodiments, the microparticle is introduced into the aqueous suspension as a lyophilized microparticle.

The subject is preferably a mammal. The mammal can include, without limitation, a human, non-human primate (such as an ape, chimpanzee), horse, cow, pig, sheep, goat, dog, or cat.

Administration of the BMP-2 microparticle, or formulations containing resolubilized microparticles, can be via any desired route. For example, administration can be local at the site at which increase in BMP-2 levels is desired.

Among the indications for which the BMP-2 microparticle, or formulations containing resolubilized microparticles, can be used are bone-related disorders. For example, a suitable subject has or is at risk for fracture of a bone. The bone can include, without limitation, tibia, oral/maxillofacial bone, or spinal bone.

Additional indications include treatment of periodontal disease, and other tooth repair processes. Such agents may provide an environment to attract bone-forming cells, stimulate growth of bone-forming cells or induce differentiation of progenitors of bone-forming cells. Further indications include osteoporosis, conditions in which increase in neuronal survival is desired, wound healing and related tissue repair. The types of wounds include, but are not limited to burns, incisions and ulcers.

Also within the invention is a method of making a population of bioactive BMP-2 microparticles. The method includes providing a first solution comprising a BMP-2 polypeptide, and mixing the first solution with a second solution with a known pH and ionic concentration that results in precipitation 
of BMP-2 polypeptide upon contact with the second solution, thereby forming a mixed first solution and second solution. The BMP-2 polypeptides are allowed to precipitate, thereby forming a population of BMP-2 microparticles.

The BMP-2 protein is preferably present in the first solution at a concentration of about 0.1 to about 20 mg/ml, e.g., about 0.5 to about 10 mg/ml, or about 0.75 mg/ml to 2.5 mg/ml. The first solution is provided at a pH of about 1.5 to 8, e.g., from about 3 to about 5, or about 4.2 to about 4.8. A particularly preferred pH is about 4.5. To facilitate mixing, the first solution can be provided as a turbulent solution when mixed with the second solution.

The final pH of the mixed first solution and second solution is preferably about 4.0 to about 10.0. A more preferred pH range is from about 5.0 to about 9.5, or about 6.0 to about 9.0. A particularly preferred final pH of the mixed first solution and second solution is about 7.4.

If desired, the BMP-2 microparticles can be concentrated. Methods of concentration can include, without limitation, centrifugation and filtration.

When a pH of about 7.4 is targeted for the combined first and second solution, the second solution is formulated so that the ionic strength of the mixed first solution and second solution is in the range of 5 to 1000 mM, more preferred from 20 to 350 mM, e.g. approximately 140 mM for the following composition: 107 mM NaCl, 27 mM $NaHCO_3$, 1.0 mM $NaH_2PO_4$, 0.5 mM $Na_2SO_4$.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

BMP-2 microparticles of the invention are formed using any convenient source of BMP-2 protein. BMP-2 proteins are known in the art and are disclosed in several patents, patent applications, publications. Representative patents include, without limitation, U.S. Pat. Nos. 5,013,649, 6,150,328, 6,187,742, and 6,190,880. The BMP-2 may be recombinantly produced, a recombinant human bone morphogenetic-2 (rh-BMP-2) protein, or purified from a protein composition. The BMP-2 may be homodimeric, or may be heterodimeric with other BMPs (including, without limitation, a heterodimer composed of one monomer each of BMP-2 and BMP-6) or with other members of the TGF-β superfamily, such as activins, inhibins and TGF-β1 (including, without limitation, a heterodimer composed of one monomer each of a BMP and a related member of the TGF-βsuperfamily). Examples of such heterodimeric proteins are described for example in Published PCT Patent Application WO 93/09229, the specification of which is hereby incorporated herein by reference. A preferred BMP-2 has the amino acid sequence of the BMP-2 polypeptide disclosed in U.S. Pat. No. 5,013,649.

A human BMP-2 protein includes the amino acid sequence and DNA sequence disclosed in FIG. 1 of U.S. Pat. No. 6,190,880 The contents of this figure are incorporated herein by reference in their entirety. Human BMP-2 proteins are further characterized as disulfide-linked dimers and homodimers of mature BMP-2 subunits. Recombinantly-expressed BMP-2 subunits include protein species having heterogeneous amino termini. One BMP-2 subunit is characterized by comprising amino acid #249 (Ser)—#396 (Arg) of FIG. 1 (see especially SEQ ID NOs. 1 and 2 in the figure) of U.S. Pat. No. 6,190,880. Another BMP-2 subunit is characterized by comprising amino acid #266 (Thr)—#396 (Arg) of FIG. 1 of U.S. Pat. No. 6,190,880. Another BMP-2 subunit is characterized by comprising amino acid #296 (Cys)—#396 (Arg) of FIG. 1 of U.S. Pat. No. 6,190,880. A mature BMP-2 subunit is characterized by comprising amino acid #283 (Gln)—#396 (Arg) of FIG. 1 of U.S. Pat. No. 6,190,880. This latter subunit is the presently most abundant protein species which results from recombinant expression of BMP-2 (FIG. 1 of U.S. Pat. No. 6,190,880). However, the proportions of certain species of BMP-2 produced may be altered by manipulating the culture conditions. BMP-2 may also include modifications of the sequences of FIG. 1 of U.S. Pat. No. 6,190,880, including, without limitation, deletion of amino acids #241-280 and changing amino acid #245 Arg to Ile, among other changes.

As described in detail in U.S. Pat. No. 6,150,328, incorporated by reference herein, human BMP-2 may be produced by culturing a cell transformed with a BMP-2 and recovering and purifying from the culture medium one or more of the above-identified protein species, substantially free from other proteinaceous materials with which it is co-produced.

Preparation of Bioactive BMP-2 Microparticles

Bioactive BMP-2 microparticles can be prepared by combining a solution containing BMP-2 and a second solution that has an ionic concentration and pH that results in precipitation of the BMP-2.

While the concentration of BMP-2 in the first solution is not critical, the concentration is preferably low enough to exclude a possible agglomeration during precipitation. On the other hand, the concentration is preferably high enough to avoid high losses of soluble BMP and to avoid forming BMP-2 particles that are insufficiently small. In some embodiments, the BMP-2 polypeptide is present in the first solution at a concentration of about 0.1 mg/ml to 20 mg/ml A preferred concentration range for the BMP-2 is 0.75 mg/ml to 2.5 mg ml If desired, the suspension can be further concentrated.

The pH of the first solution is about 1.5 to about 8, e.g. from about 3 to about 5, preferably about 4.2 to about 4.8. A referred pH is about 4.5. A preferred first solution additionally includes 5 mM L-glutamic acid, 5 mM sodium chloride, 0.5% sucrose, 2.5% glycine, 0.01% polysorbate 80 pH 4.5 The second solution has a known pH and ionic concentration that, when combined with the first BMP-2 containing solution, results in precipitation of BMP-2 polypeptide upon contact with the second solution. As the solubility of BMP is a function of the ionic strength, other salts and/or buffers, buffers with an adjusted ionic strength can be used. If the second solution is of high ionic strength, the precipitation can be performed over a wide pH range, including, without limitation, pH 4 to pH10. However, a preferred target pH, i.e., the pH of the solution resulting from mixing the first solution and the second solution, is around pH 7.4. When the second solution is provided at one-tenth the volume of the first solution, a suitable composition that increases the pH from 4.5 to a targeted value of 7.4 includes 1120 mM NaCl, 300 mM $NaHCO_3$, 11 mM $NaH_2PO_4$, 5.5 mM $Na_2SO_4$, 40 mM NaOH, and purified water, such that the total volume of the second solution is 10% of the first solution. Because precipitation is typically a time-dependent process, the mixed solutions are allowed to equilibrate for a time sufficiently long to obtain the desired microparticles.

The precipitated microparticles are preferably concentrated using methods known in the art. A preferred method is centrifugation. The centrifugation conditions are chosen so the structural integrity of the microparticles is not compromised.

Either the first solution of BMP-2 or the precipitation solution of both can contain suitable polymers including, without limitation, hyaluronic acid, collagen, carmellose sodium, polyvinyl alcohol, chitosan or cationic starch.

If desired the microparticles can be lyophilized. In general, any lyophilization method known in the art can be used. For example, lyophilization can be performed by freezing or drying. For freezing, either shock freezing or regular freezing can be used. A preferred formulation for freezing is immersion of the microparticle for 90 seconds in liquid nitrogen, after which frozen vials are stored at −80° C.

A suitable drying regimen to produce lyophilized microparticles includes a primary drying phase and a secondary drying phase. In the primary drying phase, a vial containing the BMP-2 microparticles is equilibrated to −30° C. in the absence of a vacuum. Vials are then maintained at −30° C. at 1 mbar for 24-48 hours. In the secondary drying phase, the vials are heated to 20° C. a pressure of 0.04 mbar within 2 hours, followed by an additional five hours at the same temperature and pressure.

Structural integrity of BMP-2 polypeptides can be performed using methods known in the art. For example, analysis can be performed via Fourier-Transform-Infrared-Spectroscopy. In addition, after redissolving the microparticles, gel electrophoresis, size-exclusion chromatography, reversed-phase chromatography, ion-exchange chromatography, peptide mapping can be performed to verify the structural integrity of BMP-2 polypeptides. Techniques including asymmetrical field flow fractionation can be used to determine the extent of dissolution of BMP-2 microparticles.

The BMP-2 microparticles are preferably provided in a bioactive form. By bioactive is meant that the BMP-2 polypeptide, when resolubilized, retains at least one biological activity associated with a BMP-2 polypeptide. For example, BMP-2 proteins can be characterized by the ability to induce bone formation. Human BMP-2 also has in vitro activity in the W20 bioassay (see U.S. Pat. No. 6,190,880 and reference described therein). Human BMP-2 is further characterized by the ability to induce cartilage formation. Human BMP-2 may be further characterized by the ability to demonstrate cartilage and/or bone formation activity in the rat bone formation assay described in the above-referenced application.

If desired, the BMP-2 microparticles can be provided in association with a polymeric carrier. In some embodiments the polymeric carrier is biodegradable. The polymeric carrier can be natural or synthetic.

Suitable biodegradable carriers include, without limitation, a polylactide, polylactide-co-glycolide, polyanhydride, polyorthoester, polyethylenevinylacetate, or nylon. The polymeric carriers can be formulated to provide a sustained-release matrix. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. Suitable natural polymeric carriers include, without limitation, collagen, chitosan, hyaluronic acid, and cellulose. If desired, the microparticle can contain a therapeutic amount of at least one additional bone morphogenetic protein or another agent beneficial to the treatment of the bone and/or cartilage defect, wound, or tissue in question. These agents include various growth factors such as epidermal growth factor (EGF), platelet derived growth factor (PDGF), transforming growth factor (TGF), and insulin-like growth factor (IGF).

BMP-2 microparticles of various sizes can be prepared by varying the conditions used in their manufacture. In various embodiments, the microparticle has a diameter from about 0.1 μm to about 2000 μm. For example, suitable microparticle diameters can range, without limitation, from 0.5 μm to about 1500 μm, 1 μm to about 1000 μm, 5 μm to about 750 μm, 10 μm to about 500 μm, 15 μm to about 250 μm, 25 μm to about 125 μm, and 37 μm to about 75 μm. Other suitable ranges include, without limitation, 0.5 μm to about 140 μm, 5 μm to about 85 μm, about 15 μm to about 75 μm, or about 25 μm to about 50 μm.

The size of microparticles can be assessed using methods and devices known in the art. These include, without limitation, a MASTERSIZER® X (Malvern Instruments Ltd., Malvern, United Kingdom). In some embodiments, the particle concentration is optimized for 4-5 ml sample cell volumes.

BMP-2 microparticles can be resolubilized or resuspended by placing them in an aqueous solution. A formulation buffer preferably includes sodium and ions at or near physiological concentrations. A suitable composition of an aqueous suspension includes 107 mM NaCl, 27 mM $NaHCO_3$, 1 mM $NaH_2PO_4$, 0.5 mM $Na_2SO_4$.

Pharmaceutical Compositions Including BMP-2 Microparticles and Methods of Using BMP-2 Microparticles 
BMP-2 microparticles can be used to prepare pharmaceutical compositions for treating a variety of indications. In some embodiments, the microparticles are synthesized and utilized in an aqueous suspension. In other embodiments, pharmaceutical compositions are prepared by resuspending the microparticles just prior to delivery into a subject. If desired, the BMP-2 particles can be delivered as a powder in, direct local, application to its intended site of action. The BMP-2 microparticles can additionally be delivered if desired as suspensions in other non-aqueous vehicles, including, without limitation, oils or biocompatible organic solvents.

The BMP-2 microparticle based pharmaceutical compositions and therapeutic methods of the invention utilize the resolubilization or resuspension of BMP-2 that occurs upon introduction of the BMP-2 protein into the solution. Thus, the invention includes a method of increasing bone morphogenetic protein-2 (BMP-2) levels in a subject by providing an aqueous BMP-2 suspension comprising a resolubilized or resuspended BMP-2 polypeptide, and introducing the aqueous suspension into the subject in an amount sufficient to increase BMP-2 levels in the subject. An increase in BMP-2 levels can be determined by assessing levels of BMP-2 polypeptide in the subject post-administration. BMP-2 levels can determined directly using reagents (including, without limitation anti-BMP-2 antibodies). In some embodiments, a $5\times10^2$, $1\times10^3$-fold, $1\times10^4$-fold, $1\times10^5$-fold, or $1\times10^6$-fold or more increase in BMP-2 levels occurs post-administration.

Preferably, the increase in BMP-2 protein levels is a therapeutically effective amount. Therapeutically effective amounts can be determined by identifying an improvement in a condition known to benefit from treatment with a BMP-2 protein. For example, BMP-2 proteins are further characterized by the ability to induce the formation of cartilage and/or bone, and by their ability to demonstrate cartilage and/or bone formation activity in the rat bone formation assay described in U.S. Pat. No. 5,066,058. In preferred embodiments, the proteins of the invention demonstrate activity in this rat bone formation assay at a concentration of 0.5 μg-100 μg/gram of bone. In more preferred embodiments these proteins demonstrate activity in this assay at a concentration of 1 μg-50 μg/gram of bone. More particularly, these proteins may be characterized by the ability of 1 μg of the protein to score at least +1 in the rat bone formation assay described in Example III using the modified scoring described in Example VII of U.S. Pat. No. 5,066,058.

The aqueous suspension containing BMP-2 protein resuspended or resolubilized from a BMP-2 microparticle can be prepared by introducing into an aqueous solution a microparticle comprising a precipitated bioactive bone morphogenetic protein 2 (BMP-2) and allowing the precipitated BMP-2 protein to resolubilize.

In other embodiments, the microparticle is introduced into the aqueous suspension as a lyophilized microparticle.

The BMP-2 microparticles and suspensions thereof can be used in methods and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a BMP-2 polypeptide delivered from a microparticle in admixture with a pharmaceutically acceptable vehicle, carrier or matrix. It is expected that BMP-2 polypeptide released from microparticles may act in concert with or perhaps synergistically with other related proteins and growth factors.

The BMP-2 microparticle can be used along with a therapeutic amount of at least one additional bone morphogenetic protein. Further, BMP-2 microparticles may be combined with other agents beneficial to the treatment of the bone and/or cartilage defect, wound, or tissue in question. These agents include various growth factors such as epidermal growth factor (EGF), platelet derived growth factor (PDGF), transforming growth factor (TGF), and insulin-like growth factor (IGF). The preparation and formulation of such physiologically acceptable protein compositions, having due regard to pH, isotonicity, stability and the like, is within the skill of the art. The therapeutic compositions are also presently valuable for veterinary applications. Particularly domestic animals and thoroughbred horses in addition to humans are desired patients for such treatment with pharmaceutical compositions that include BMP-2 microparticles or formulations prepared from the microparticles.

Additional indications include treatment of periodontal disease, and other tooth repair processes. Such agents may provide an environment to attract bone-forming cells, stimulate growth of bone-forming cells or induce differentiation of progenitors of bone-forming cells. Further indications include osteoporosis, conditions in which increase in neuronal survival is desired, wound healing and related tissue repair. The types of wounds include, but are not limited to burns, incisions and ulcers. (See PCT Publication WO84/01106 incorporated by reference herein for discussion of wound healing and related tissue repair).

The therapeutic method includes administering the BMP-2 microparticles (or formulations prepared from resuspended BMP-2 microparticles). A pharmaceutical composition of the invention is formulated to be compatible with its intended route of administration. Administration modes are chosen based on the bioactive agent and the intended site of application. When resolubilized or resuspended the use of BMP-2 particles can be systemic or local. Examples of routes of administration include local, parenteral, including, without limitation, intravenous, intradermal, subcutaneous, oral (such as inhalation), transdermal (i.e., topical), transmucosal, and rectal administration. Solutions or suspensions used for local, parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, agents for the adjustment of tonicity such as sodium chloride or dextrose, and surfactants such as Cremophor EL, polysorbate 20, polysorbate 60, or polysorbate 80. The pH can be adjusted with acids or bases, such as hydrochloric acid or sodium hydroxide. The parenteral preparation can be enclosed in ampoules, disposable syringes or multiple dose vials made of glass or plastic. When administration is systemic, the BMP-2 microparticle, or composition containing or derived from a BMP-2 microparticle may additionally include an associated material that facilitates targeting to and/or retention at a desired site in the subject.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (including, without limitation, a BMP-2 protein resolubilized or resuspended from a BMP-2 microparticle) in the required amount in an appropriate solvent with one or a combination of ingredients enumerated above, as required, followed by filtered sterilization.

The pharmaceutical compositions can be included in a container, pack, or dispenser together with instructions for administration.

Oral compositions containing a resuspended or resolubilized bioactive agent generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration of the bioactive agent by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal administration. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

When administered, the pharmaceutical composition for use in this invention is typically delivered in a pyrogen-free, physiologically acceptable form. Further, the composition may desirably be encapsulated or injected in a viscous form for delivery to the site of bone cartilage or tissue damage. Local administration may be suitable for wound healing and tissue repair. Preferably for bone and/or cartilage formation, the composition includes a matrix capable of delivering BMP protein to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the BMP-2 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-2 protein. These factors include, without limitation, the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution. The addition of other known growth factors, such as IGF I (insulin like growth factor I), to the final composition, may also effect the dosage. Progress can be monitored by periodic assessment of bone growth and/or repair. One method of assessing bone growth or repair is by x-ray imaging.

The invention will be further illustrated in the following non-limiting examples.

EXAMPLE 1

Preparation of BMP-2 Microparticles

A BMP-2 microparticle is prepared by mixing a first solution containing BMP-2 protein with a second, precipitating solution.

The first solution includes rhBMP-2 at a concentration of 0.1 to 2 mg/ml and is at pH 4.5. The second solution is formulated so that upon being added at one-tenth volume (relative to the volume of the first solution), the BMP-2 protein will precipitate and the final pH of the combined solution is pH 7.4. The second solution includes 1120 mM NaCl, 300 mM $NaHCO_3$, 11 mM $NaH_2PO_4$, 5.5 mM $Na_2SO_4$, 40 mM NaOH and purified water.

The precipitation is performed by adding 10% (volume/volume) of a precipitating solution which contains both physiological salt and pH adjustment. The precipitation is performed in sterile tubes (15 or 50 ml), depending on the required volume. The filling of the 50 ml tube with BMP stock solution is limited to 30 ml to have enough space for the creation of a turbulent solution by using the vortex.

To achieve a quick and homogeneous distribution, a turbulent BMP bulk solution is created with the help of the vortex 10 seconds prior, while and 10 seconds after the addition of the precipitation solution. In addition in the 50 ml tube batches the original cap is replaced against a cap with a centered whole of approximately 3 mm diameter to pipette the precipitation solution. After adding the precipitation solution, the tube is sealed with the original cap, and equilibrated for the desired length of time (see Example 2).

The BMP-2 microparticles are then concentrated by centrifugation, after which they are lyophilized.

EXAMPLE 2

Assessment of BMP-2 Microparticle Size

BMP-2 microparticle diameter was assessed using a MALVERN MASTERSIZER X® instrument (Malvern Instruments Ltd., Malvern, UK) with a sample cell designed for volumes of 4 to 5 ml. Mixing of a rhBMP-2 solution with a stock solution was used to generate physiologic salt concentrations.

Figure 1:
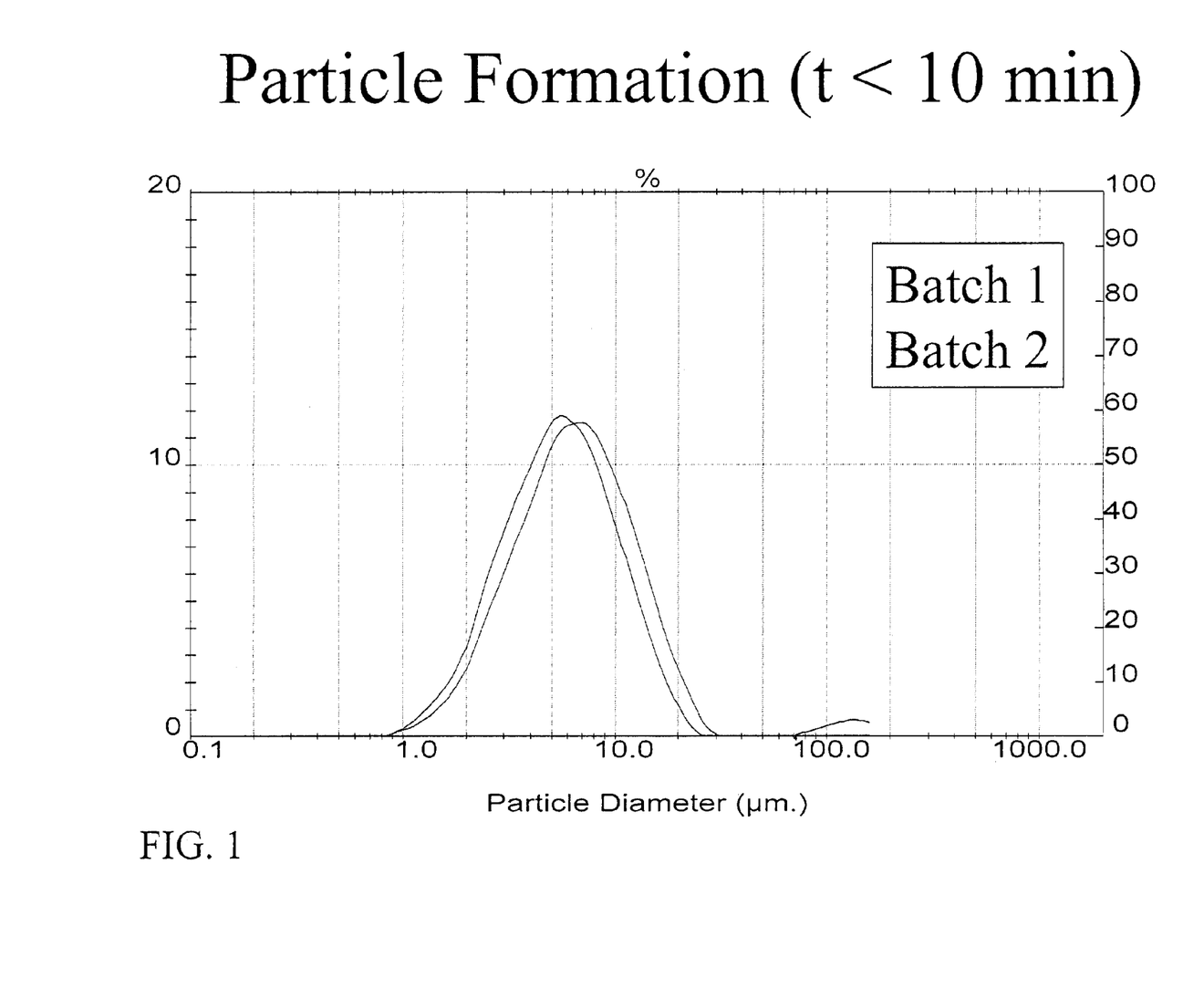
FIG. 1 is a graph showing particle diameter distributions in BMP-2 microparticles formed during a formation period of less than ten minutes.
Figure 2:
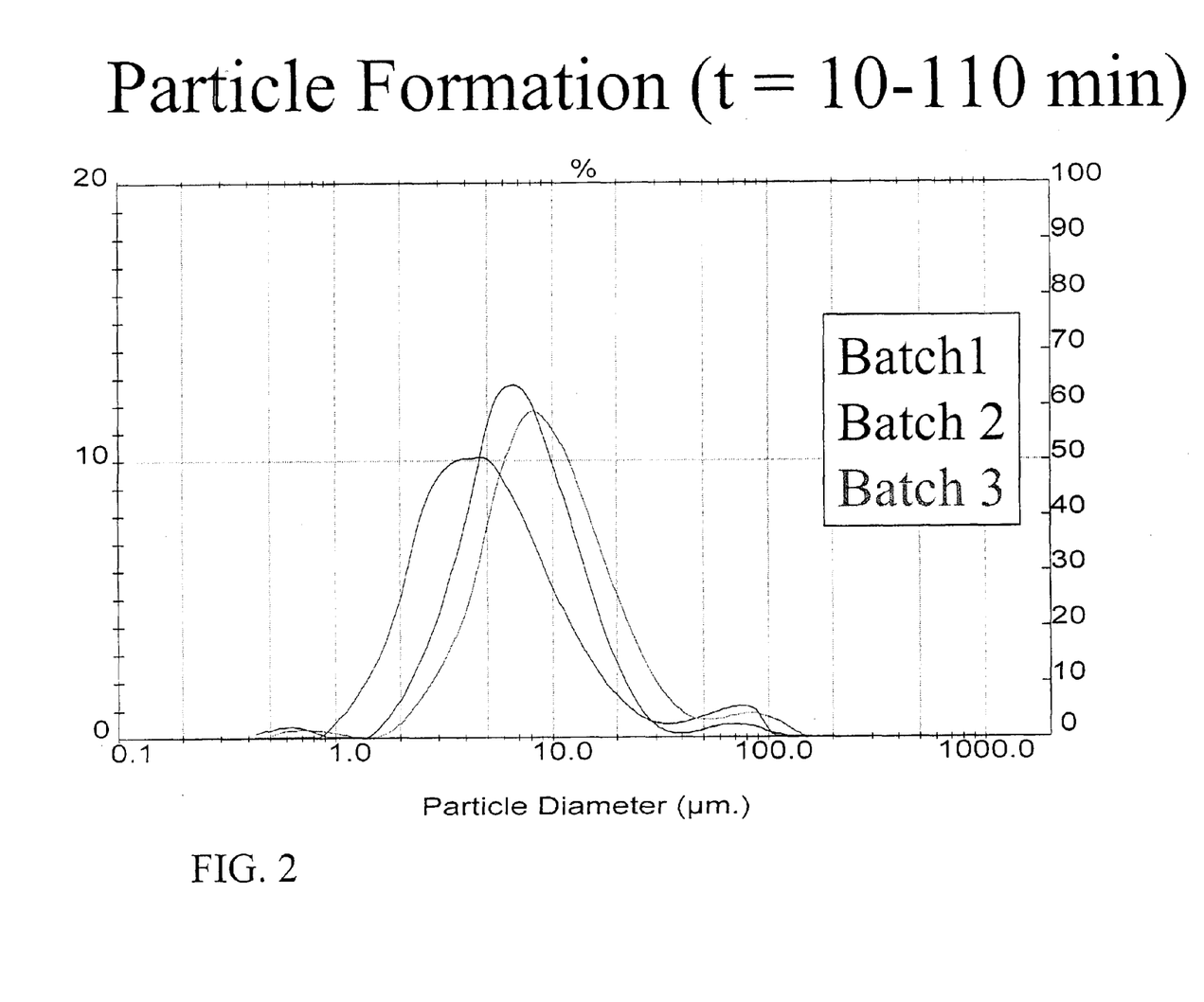
FIG. 2 is a graph showing particle diameter distributions in BMP-2 microparticles formed during a formation period of 10 to 110 minutes.
Figure 3:
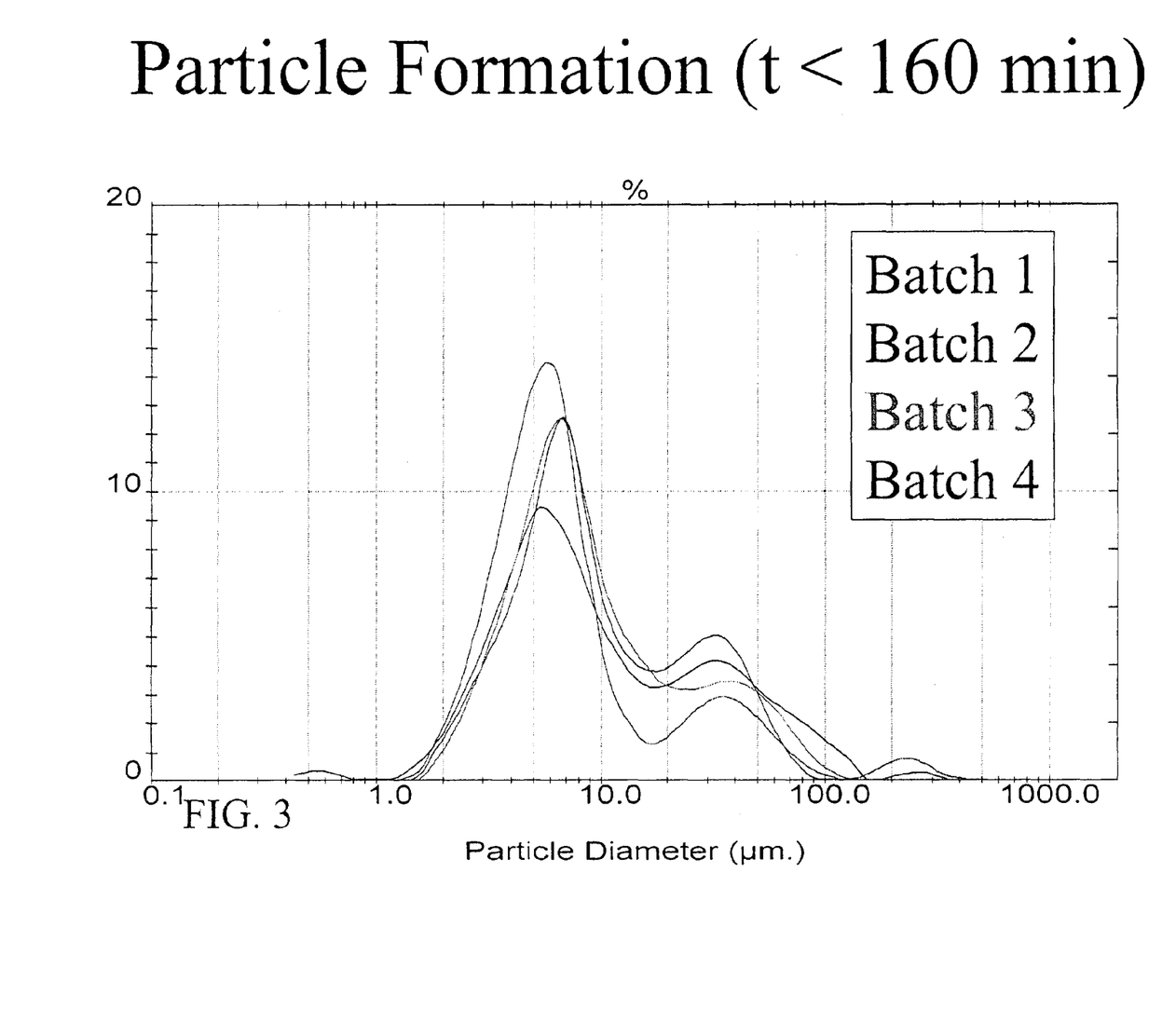
FIG. 3 is a graph showing particle diameter distributions in BMP-2 microparticles formed during a formation period of up to 160 minutes.

The range in particle diameter in populations of microparticles subjected to equilibration for various lengths of time is shown in FIGS. 1-3. FIG. 1 shows the size distribution obtained in two batches microparticles equilibrated for less than ten minutes. Most particles are smaller then 10 µm in diameter, with a peak detected for microparticles of 5 µm to 6 µm in diameter.

FIG. 2 shows the size distribution obtained for three batches of microparticles equilibrated for between 10 and 110 minutes. While 6 µm to 9 µm are the most common size ranges, a higher number of microparticles with diameters greater than 10 µm are detected as compared to the distribution observed in FIG. 1.

FIG. 3 shows the results using four batches of particles equilibrated for up to 160 minutes. While the most common size ranges are again 6 µm to 9 µm, a second peak is detected in the 30 µm to 40 µm size range.

These results demonstrate microparticles were obtained in these studies in the range of 1-100 µm and demonstrated a bimodal distribution with maxima at approximately 6±1 µm and 31±5 m.

Figure 4:
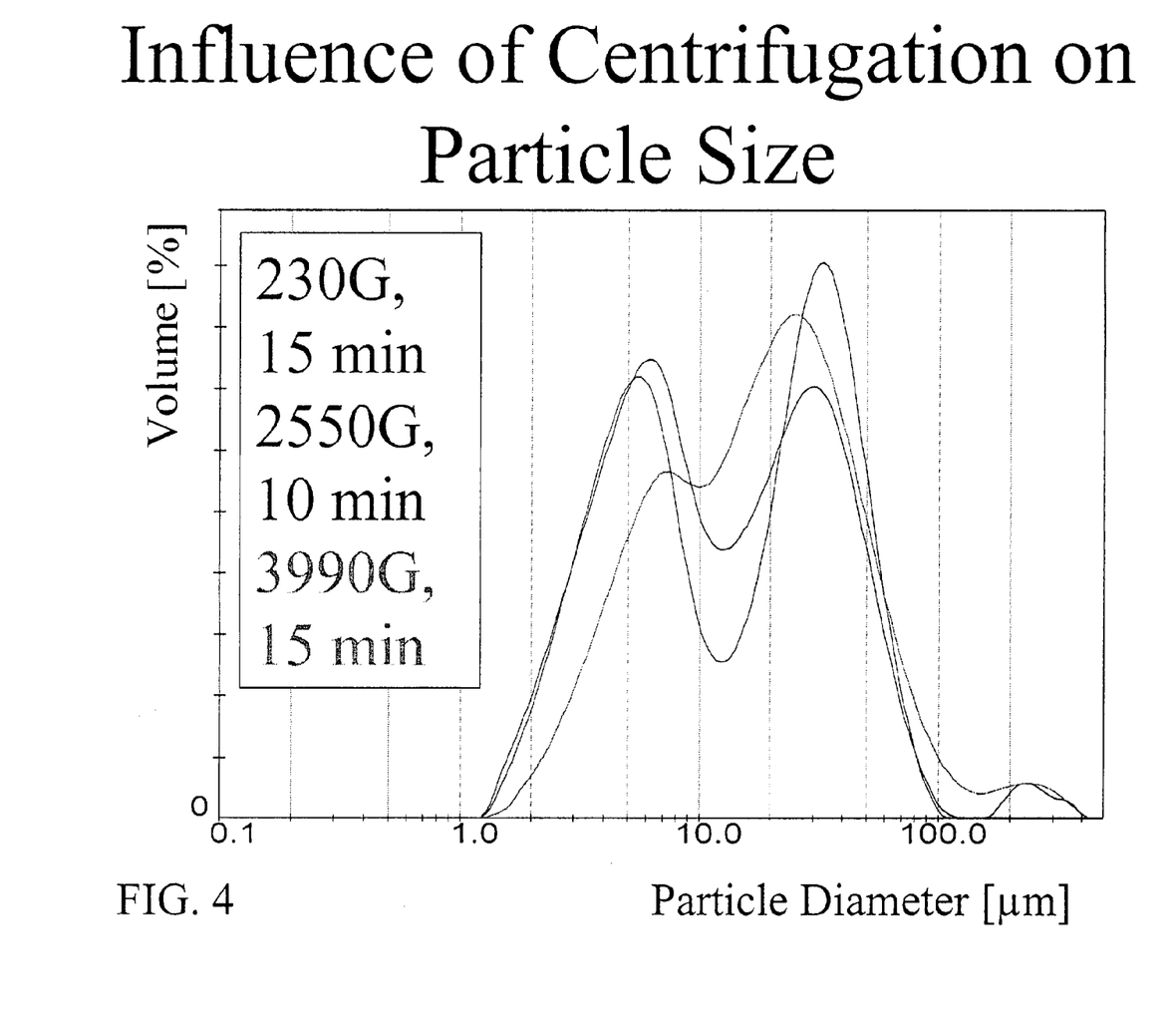
FIG. 4 is a graph showing the influence of centrifugation on BMP-2 particle diameter.

The influence of centrifugation on particle size was determined. The results are shown in FIG. 4 following centrifugation under three conditions: 230 G for 15 minutes; 2550 G for 10 minutes, or 3990 G at 15 minutes. In these studies, particle size was only slightly affected by subsequent centrifugation.

Figure 5:
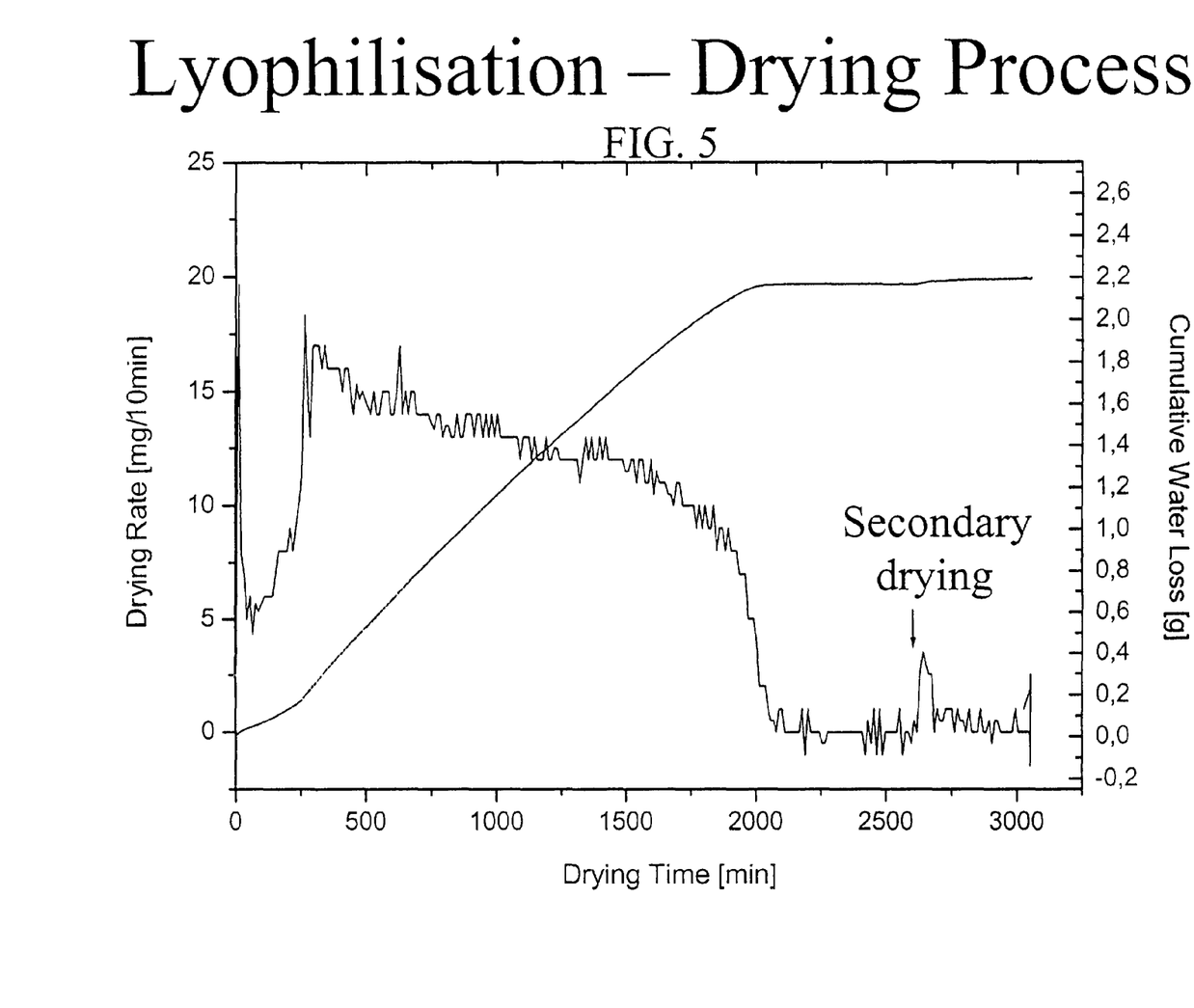
FIG. 5 are graphs showing the rate of drying and cumulative water loss over time in microparticles subjected to lyophilization.
Figure 6:
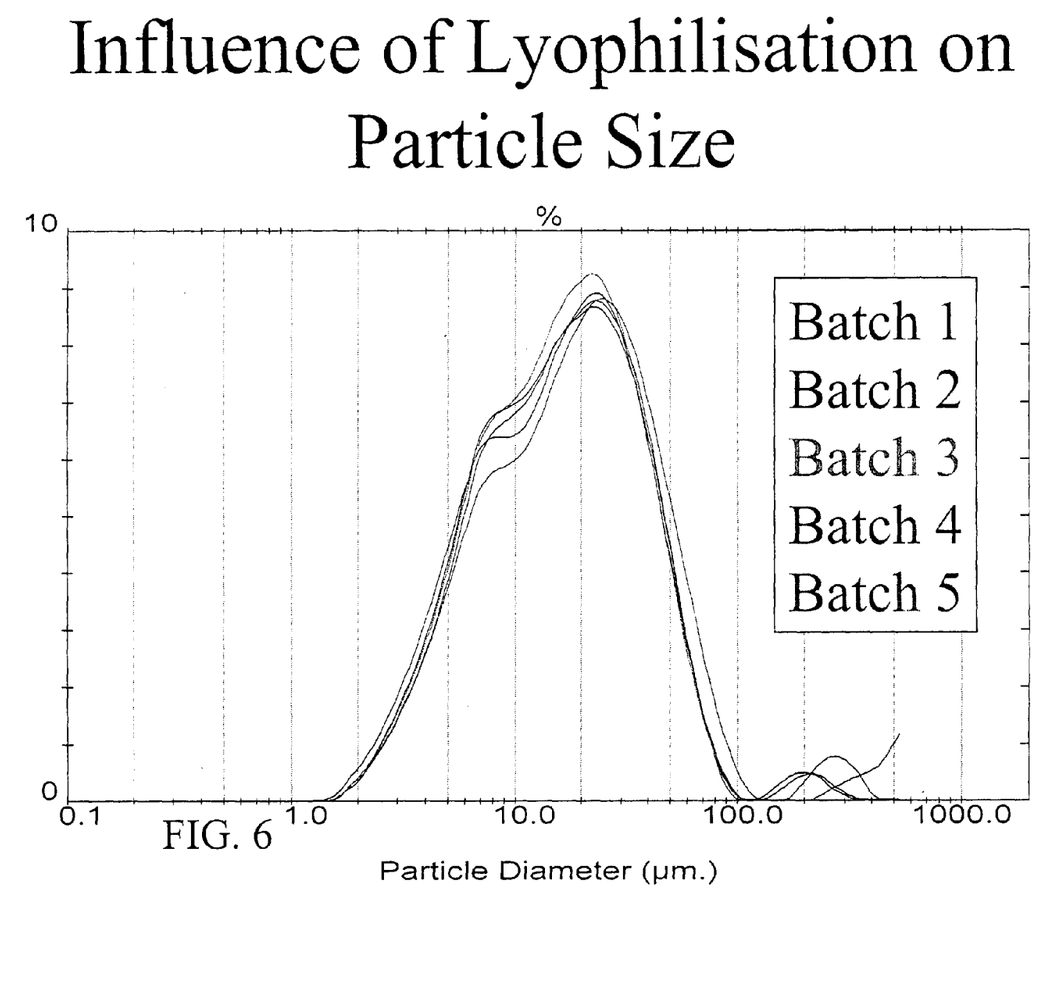
FIG. 6 is a graph showing the influence of lyophilization on BMP-2 particle diameter

The effect of lyophilization on microparticle size was examined. The extent of lyophilization was assessed by measuring the drying rate and cumulative water loss. The extent of lyophilization is shown in FIG. 5. The effect of lyophilization on particle size is shown in FIG. 6. Lyophilization induced a change to a broad monomodal distribution with d50 and d90 values of 35 µm and 85 µm, respectively.

Figure 7:
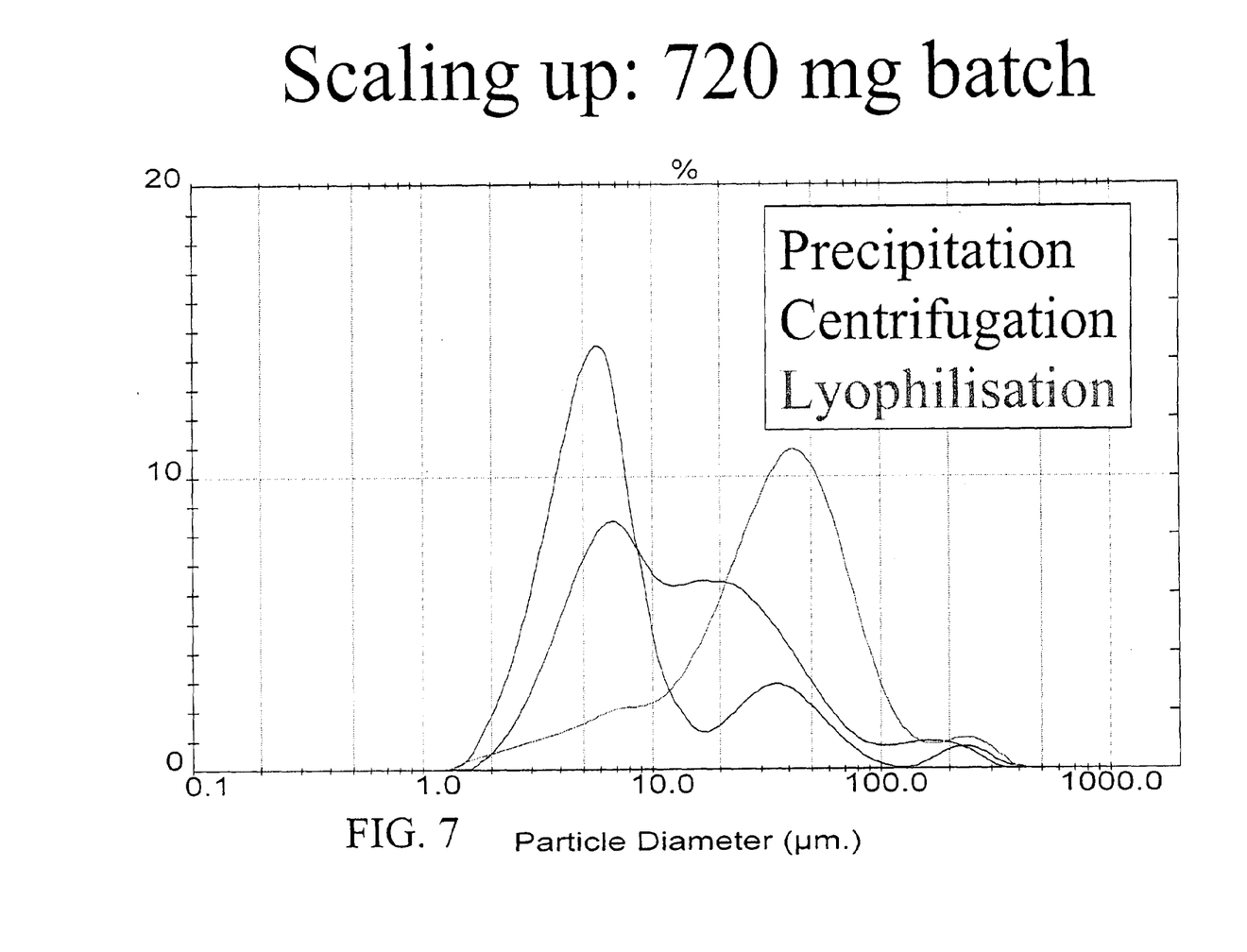
FIG. 7 is a graph showing particle diameter distributions on 720 mg BMP-2 microparticle preparations.

The particle size obtained using a solution containing a larger amount (720 mg) of protein was examined. Particle size was determined following precipitation, centrifugation, and lyophilization. The results are shown in FIG. 7. Centrifugation and lyophilization induced changes in microparticle diameter as compared to diameter in microparticles that were subjected only to precipitation.

Figure 8:
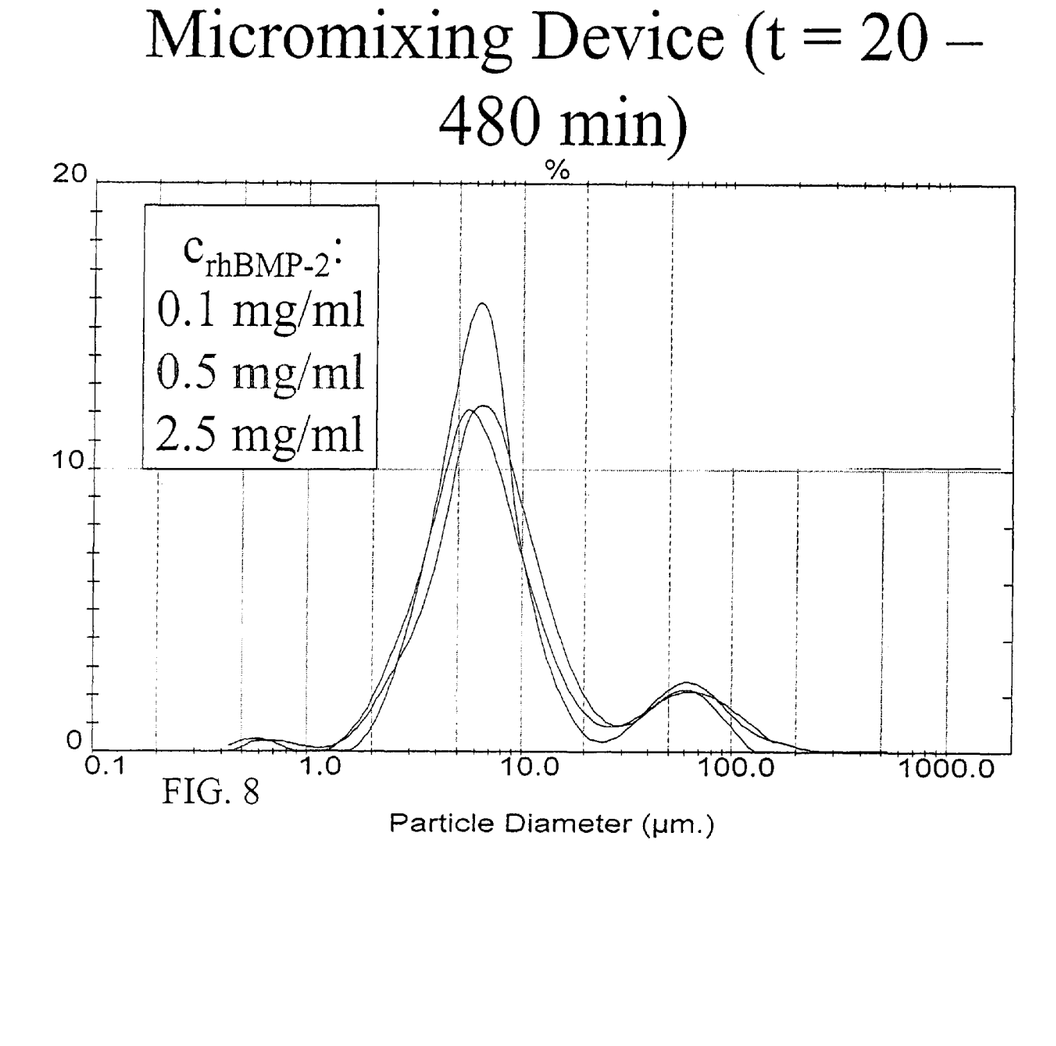
FIG. 8 is a graph showing diameter distributions in BMP-2 microparticles prepared using a micromixing device.

Mixing of BMP-2 containing solution and precipitation solution was performed using an interdigital single mixing device (MICROMIXER® device, Institut für Mikrotechnik, Mainz, Germany). This device allows the combination of small volumes using diffusion through thin-walled lamellae. Equilibration was performed for 20-480 minutes using BMP-2 concentrations of 0.1 mg/ml, 0.5 mg/ml, and 2.5 mg/ml. The diameter distribution is shown in FIG. 8. For all three concentrations, a bimodal size distribution was obtained with peaks around 6-9 µm and a second, broader distribution centered around 40-60 µm.

The integrity of the protein was analysed following dissolution of the microparticles. BMP-2 was found to be intact following dissolution.

Other Embodiments

The descriptions given are intended to exemplify, but not limit, the scope of the invention. While the above invention has been described with reference to BMP-2, it is understood that the methods described herein can be used to make microparticles for other bioactive agents, and pharmaceutical compositions based on these microparticles. These bioactive agents include, without limitation, additional bone morphogenetic proteins, members of the Transforming Growth Factor-β superfamily. The methods can also be used to make microparticles comprising therapeutic polypeptides that have solubility and pI properties similar to BMP-2.

What is claimed is:

1. A method of making a population of bioactive bone morphogenetic protein-2 (BMP-2) microparticles, the method comprising providing a first solution comprising a BMP-2 polypeptide at a concentration of about 0.75 mg/ml to 2.5 mg/ml and a pH of about 4.2 to about 4.8; mixing said first solution with a second solution with a known pH and ionic concentration that results in precipitation of BMP-2 polypeptide upon contact with said second solution, thereby forming a mixed first solution and second solution; and allowing BMP-2 polypeptides to precipitate, thereby forming a population of BMP-2 microparticles.

2. The method of claim 1, further comprising concentrating said BMP-2 microparticles.

3. The method of claim 1, wherein the first and second solutions are mixed in a relative volume of ten to one.

4. The method of claim 1, wherein the first solution has a pH of about 4.5.

5. The method of claim 1, wherein the first solution is a turbulent solution when contacting the second solution.

6. The method of claim 1, wherein the mixed first solution and second solution has a pH of about 4.0 to about 10.0.

7. The method of claim 1, wherein the mixed first solution and second solution has a pH of about 7.4.

8. The method of claim 1, wherein the mixed first solution and second solution is 107 mM NaCl, 27 mM NaHCO$_3$, 1.0 mM NaH$_2$PO$_4$, 0.5 mM Na$_2$SO$_4$.

9. The method of claim 1, wherein the mixed first and second solution have an ionic strength from about 5 mM to about 1000 mM.

10. The method of claim 1, wherein the mixed first and second solution have an ionic strength from about 20 mM to about 250 mM.

11. The method of claim 1, wherein the mixed first and second solution have an ionic strength of about 140 mM.

12. A method of increasing BMP-2 levels in a subject, the method comprising providing an aqueous BMP-2 suspension comprising a resolubilized precipitated bioactive BMP-2 polypeptide; and introducing said aqueous suspension into said subject in an amount sufficient to increase BMP-2 levels in said subject, wherein said resolubilized precipitated bioactive BMP-2 polypeptide is resolubilized from a BMP-2 microparticle made by a method comprising providing a first solution comprising a BMP-2 polypeptide at a concentration of about 0.75 mg/ml to 2.5 mg/ml and a pH of about 4.2 to about 4.8;

mixing said first solution with a second solution with a known pH and ionic concentration that results in precipitation of BMP-2 polypeptide upon contact with said second solution, thereby forming a mixed first solution and second solution; and allowing BMP-2 polypeptides to precipitate, thereby forming a population of BMP-2 microparticles.

13. A method of preparing a population of bioactive BMP-2 microparticles, the method comprising:

providing a first solution comprising BMP-2 polypeptides;

mixing said first solution with a second solution with a known pH and ionic concentration that results in precipitation of BMP-2 polypeptide upon contact with said second solution, thereby forming a mixed first solution and second solution; wherein the mixture is equilibrated for a time period ranging from 10 minutes to 480 minutes and allowing BMP-2 polypeptides to precipitate, thereby forming a population of BMP-2 microparticles having a diameter ranging from 5 μm to 85 μm.

14. The population of bioactive BMP-2 particles having a diameter ranging from 5 μm to 85 μm prepared by the method of claim 13.

* * * * *